United States Patent
Gergely et al.

(10) Patent No.: US 7,836,851 B2
(45) Date of Patent: Nov. 23, 2010

(54) FORMULA AND METHOD FOR TREATING WATER IN FISH TANKS

(76) Inventors: Anthony Gergely, P.O. Box 590, Seguin, TX (US) 78156; Lane Gergely, P.O. Box 590, Seguin, TX (US) 78156

( * ) Notice: Subject to any disclaimer, the term of this patent is extended or adjusted under 35 U.S.C. 154(b) by 325 days.

(21) Appl. No.: 12/154,380

(22) Filed: May 22, 2008

(65) Prior Publication Data

US 2009/0288611 A1    Nov. 26, 2009

Related U.S. Application Data

(60) Provisional application No. 60/931,330, filed on May 23, 2007.

(51) Int. Cl.
*A01K 63/02* (2006.01)
(52) U.S. Cl. ...................................................... 119/201

(58) Field of Classification Search .................. 119/200, 119/201, 203, 204, 205, 215, 245, 268
See application file for complete search history.

(56) References Cited

U.S. PATENT DOCUMENTS

| 4,619,943 | A | * | 10/1986 | Rao | 514/464 |
| 5,174,998 | A | * | 12/1992 | Ijitsu et al. | 424/410 |
| 7,351,739 | B2 | * | 4/2008 | Ho et al. | 514/475 |

* cited by examiner

*Primary Examiner*—Thomas Price

(57) ABSTRACT

A formula and method for treating water used to hold captive fish in tanks includes isoeugenol, sodium chloride, potassium chloride and soluble dextrose. Also included are an ammonia remover, a chlorine remover, a bacterial and fungal spore remover, an anti-columnaris and saprolegnia agent, a disinfectant, a slime-coating protecting agent, a chelating agent and a surface foam remover.

22 Claims, No Drawings

FORMULA AND METHOD FOR TREATING WATER IN FISH TANKS

CROSS REFERENCE TO RELATED APPLICATION

This application claims the benefit of Provisional U.S. Patent Application 60/931,330 filed May 23, 2007.

STATEMENT REGARDING FEDERALLY-FUNDED RESEARCH AND DEVELOPMENT

The invention described in this patent application was not the subject of federally-funded research or development.

FIELD

This invention relates to a chemical water conditioning formula and method to enhance the survivability of brood stock game fish, aquarium fish and bait fish during holding and transportation in portable water containers, water raceways and permanent water holding tanks.

BACKGROUND

There are many factors, which must be taken into consideration when holding or transporting fish in captivity in a water tank. Fish are dependent on the water in which they swim along with the chemistry of the water to sustain life. It is a known fact that fish respond stressfully to being held in captivity and even more so when a tank is crowded with other fish. Severe losses of captive fish will result from this stress placed upon the fish unless the condition of the water in the tank is chemically changed to enhance the ability of the water in the tank to support fish life.

After 25 years of research by the inventors named herein into the question of why the life expectancy of fish is dramatically shortened during captivity, numerous experiments have been conducted to counter the effects of stress upon fish held in tanks. Water parameters have been studied and the identified water parameters have been assessed to understand the effect of each water parameter on stress and eventually on the mortality of the fish. The assessed parameters include, but were not limited to, the effects of osmotic balances between the water and the fish's internal ionic balance, the effect of replenishing ammonia, the effect of reducing stress, the effects of reducing bacteria, fungal spores and viruses, the effect of replenishing the natural slime coating on the fish, the effect of eliminating chlorine and/or chloramines, the effect of eliminating heavy metals, the effect of eliminating pesticides and the effect of retarding the formation of surface water foam.

Other variables affecting the mortality of fish were found to include the presence of invasive species acquired during the fish transportation process, wherein such invasive species may be inadvertently contained within the water in the fish tank by way of the source of the water from a lake or river.

Live fish are held and transported in tanks for many reasons. Some live fish are transported back to hatcheries to obtain eggs and milt for spawning purposes. Other live fish are used in the aquarium trade after capture. Some live fish are transported through a distribution system for the sole purpose of eventually using those fish as live bait to catch other fish on a hook and line. Still other live fish are held in captivity for the enjoyment of tournament anglers to determine who can land the heaviest catch during a day of competitive fishing. These examples are not totally inclusive of the reasons why people transport live fish, but the examples serve the purpose of explaining why people desire that fish stay alive during captivity and remain alive should they be released or held for extended periods of time captive in a water tank.

A need remains in the art for a formula and method for treating the water in a fish tank which makes it simple for both trained and novice fish handlers to properly condition the water in a fish tank thereby increasing the ability of fish handlers to maintain the lives of fish held in captivity.

SUMMARY

From the aforementioned research into the mortality of fish held in captivity, it has been discovered that the stress-causing parameters on live fish in captivity can be addressed chemically with proper dosage rates of selected chemicals. Specifically, a water conditioning compound can be formulated, manufactured and provided to handlers of live fish in an enclosed container to prolong the life of the fish contained therein.

According to the present invention a formula and method for treating water in fish tanks is disclosed which enables fish handlers to properly condition the water in fish tanks and thereby increase the ability of the fish handler to maintain the lives of fish held in captivity in a water tank.

According to the present invention the live fish are sedated during captivity to reduce stress. By sedating the fish, the fish do not fight captivity, the fish require less oxygen and the fish have less ability to injure each other. Also under sedation, larger masses of fish may be held in less volume of water than is normally attainable.

According to the present invention, the electrolyte losses of the fish due to the stress of being caught are properly handled and contained. Fish lose ions through their semi-permeable gill membranes. This loss of ions can cause the fish to experience osmotic shock if these ions are not replenished.

Further, according to the present invention harmful ammonia, a by-product of fish waste material, which ultimately will burn fish gills and render the fish gills useless for the absorption of oxygen is substantially reduced or removed.

Still further, according to the present invention, bacterial, fungal and viral loads must be subdued in the water. Subduing bacterial, fungal and viral loads in water is another part of the present invention which keeps the fish from becoming infected from diseases due to the tight and crowded containment conditions found in a fish holding or transport tank.

Yet further, according to the present invention the natural anti-bacterial slime coating of the fish is replenished. The interference of slime coat production by a fish is a result of stress. Slime coating may also be removed from the abrasion of nets, handling by dry human hands, and by contact with the floor of a boat particularly if the boat floor is carpeted.

And further, according to the present invention is the total detoxification of chlorine and/or chloramines in the holding or transport tank water. Chlorine and/or chloramines may be present in the fish holding or transportation tank because of the use of city municipality-treated water and/or ice. Both chlorine and/or chloramines can burn the gills of the live fish and render the fish gills useless for absorbing oxygen thus leading to death of the fish.

And still further, according to the present invention, heavy materials and/or pesticides are removed from the holding or transportation water. The presence of these elements and/or chemicals can cause irreversible damage to the immune system and/or internal organs of the fish, thus resulting in a delayed death of the fish following release back into open water.

And yet further, according to the present invention is the eradication of evasive species organisms from the transportation or holding water to eliminate the possibility of cross-contamination between separate bodies of water. An example of evasive species organisms would be viruses and mussels.

Finally, according to the present invention is the hindrance of surface foam development on the water in the transportation or holding tank. If foam is allowed to form and persist on the surface of the transporting or holding water, the foam acts as a barrier against oxygen transfer from air to water and can lead to hypoxia in the fish.

DESCRIPTION OF THE EMBODIMENTS

According to the research and development, which lead to the disclosed invention, a complete water conditioning mixture which maintains and stabilizes captive live fish by incorporating a selected array of chemicals into a single compound, which chemicals work together synergistically to enhance water's ability to keep fish alive in captivity, has been developed. Those of ordinary skill in the art will understand that the proportions of the identified chemicals are described below in parts per million ("ppm") by weight.

The first key ingredient of the chemical mixture for treating the water in fish tanks of the present invention is isoeugenol (2-Methoxy-4-propenylphenol; 4-hydroxy-3-methoxy-1-propenylbenzene; 4-propenylguaiacol) $C_{10}H_{12}O_2$. Isoeugenol is an essential oil derived from oil of clove that has anesthetizing capabilities for fish in water. In the preferred embodiment, the formula for maintaining the life of fish contains about 43 ppm±10% of isoeugenol to slow the metabolism of captive live fish. Greater dosage levels of isoeugenol may be added to the water in which the fish are held and have been studied; however, a dosage rate of about 43 ppm±10% isoeugenol has proven to slow down fish activity sufficiently to allow handling of the live fish. Indeed, overdoses up to 10 times the preferred amount of isoeugenol in the disclosed embodiment may be applied; however, some fish may still roll over and lose equilibrium. Although not harmful to the fish, this event may cause concern for those not familiar with fish behavior.

The benefits of treating the water in which fish are held or transported with isoeugenol are threefold. First, the metabolism of the fish is slowed and therefore the fish require less oxygen. The result is that more live fish may be held in smaller volumes of water. Also, live fish with a slower metabolism are easier to handle and fewer injuries are sustained by the fish. Because the fish are subdued, they fight captivity to a lesser degree and therefore do not injure other fish held with them in the holding or transport tank. By calming the metabolism of fish, it has been observed that hook wounds appear to coagulate faster because the flow of blood to the hook wounds is reduced.

The second advantage to the use of isoeugenol is the stimulation of the immune system of the fish. Fish held in water treated with isoeugenol respond with a normal immune system response, which normal immune system response allows the fish to fight off bacterial and viral infections to a greater degree than before they were placed in water containing isoeugenol. This response to isoeugenol is key in maintaining a healthy fish upon release as oftentimes fish released after containment will become diseased due to the stress of containment.

The third advantage to the use of isoeugenol is the suppressive effects of this essential oil on cortisol, glucose and lactate levels. By reducing these blood-born stress responders in the fish, the health of the fish is maintained while in captivity.

Fish lose electrolytes during a period of stress such as during netting, catching and captivity. Their muscles utilize these electrolytes when attempting to flee from being caught and these electrolytes must be replaced if normal fish organ functions are to resume. Therefore, both Sodium Chloride (NaCl) and Potassium Chloride (KCl) have been added to the disclosed formula to help the fish replace these lost electrolytes by way of osmotic activity through their gills. The preferred embodiment of the formula contains about 3647 ppm±10% of sodium chloride and about 1458 ppm±10% of potassium chloride in ionic presentation. These ions help stop osmotic shock and reduce stress in the fish.

The replacement of lost electrolytes is also beneficial to the slime coat production on the fish. Replacement of the lost electrolytes has resulted in the generation or replacement of the slime coat of fish held in a tank. The slime coat is essential to the health of the fish as it serves as an antimicrobial barrier.

Another essential agent which allows the fish to regain lost energy from struggling on hook and line or during the netting process is soluble dextrose. Accordingly, about 310 ppm±10% of soluble dextrose is included in the disclosed formula to help the fish regain energy.

Still another advantage to the incorporation of electrolytes, soluble dextrose and the use of the calming agent isoeugenol in the disclosed formula is that the fish are stable to the extent that they do not regurgitate undigested food contents from their stomachs. Minimizing or eliminating the regurgitation of undigested food by fish is critical for keeping the water for transporting the fish from being fouled from the regurgitated food and also preserves the body weight of the live fish during fishing tournaments.

Live fish in captivity will cause ammonia levels in the water in a holding or transport tank to rise. The presence of ammonia in the water causes fish gills to burn to an extent that the fish can no longer absorb oxygen from the water. Therefore, ammonia must be removed as it is created. To remove the ammonia, sodium formaldehyde bisulfate ($CH_3NaO_4S$) is used in the disclosed formula at a concentration of about 456 ppm±10% to eliminate ammonia by way of the hydroxymethane-end of the molecule reacting with $NH_3$ to form a non-toxic and stable water-soluble substance rendering the ammonia harmless to the fish. Furthermore, sodium formaldehyde bisulfite will also render chloramines harmless in the case where city water and/or ice used. If city water and/or ice is used in the containment vessel for holding the fish the fish may be exposed to chloramines.

In the case where city water and/or ice is used in the captivity tank, harmful chlorine may be present, which chlorine will burn fish gills if not removed. Therefore, sodium thiosulfate ($Na_2O_3S_2$), a proven chlorine remover, has been added to the disclosed formula at a rate of about 176 ppm±10%. Sodium thiosulfate converts chlorine into chloride ions, which chloride ions are available to the fish to utilize. Another advantage to using sodium thiosulfate in the disclosed formula occurs when the water vessel contains an electronic ozone converter. Ozone converters create chlorine when in the presence of sodium chloride, the chlorine is harmful to the fish. Sodium thiosulfate converts the chlorine back into chloride ions, which as previously indicated are useful to the fish.

Viruses, bacterium and fungus cause stressed and captive fish to become susceptible to disease organisms. Accordingly, several ingredients are included in the disclosed formula to help fight off these disease organisms. Included are the following agents: methylene blue (3,7-Bis(dimethylamino)-phenazathionoium chloride) $C_{16}H_{18}ClN_3S$ at a rate of about 2 ppm±10% to help kill bacterium and fungal spores. Methylene blue is also useful as a substitute oxygen donor in the case of respiratory distress.

Also included as a disease-fighting agent is Acriflavine, 3,6-Diamono-10methylaacrudinium chloride mixture with 3,6-acridinediamine, is added at a dosage rate of about 0.75 ppm±10%. This medical dye is effective against columnaris and saprolegnia diseases of fish.

To help kill viruses in the containment water, about 4.1 ppm±10% of benzalkonium chloride has been added to the disclosed formula. This disinfectant is useful in destroying viruses such as the Largemouth Bass Virus (LMVB), Viral Hemorrhagic Septicemia (VHS), and other viruses known to affect fish. The use of benzalkonium chloride is particularly important because if one fish in a holding or transport tank is infected, the use of a disinfectant such as benzalkoaium chloride will keep the other fish from becoming infected via shead viral particles in water.

Povidone-iodine (1-Ethenyl-2-pyrrolidinone homopolymer compounded with iodine) is added at a rate of about 10.25 ppm±10%. Povidone-iodine is effective as a disinfectant, a viruscide and as a bactericide.

To help protect the antibacterial static slime coating of the fish and further enhance anti-bacterial growth in the water about 2.1 ppm±10% of aloe vera is included in the disclosed formula.

Heavy metals and pesticides are removed from the water in the vessel by way of chelation. A proven chelating agent is included in the disclosed water conditioning formula by adding EDTA (Tetrasodium ethylenediaminetetraacetate) in an amount of about 8.5 ppm±10%. This chelating agent is very helpful to the fish if water heavy in metal ions such as mercury, lead, etc. is used or if water containing runoff from agricultural areas is used.

Invasive species such as viruses have been addressed by the use of benzalkonium chloride and Povidone-iodine. The eradication of invasive mussels, such as the Zebra mussel and Quagga mussel, is accomplished by the use of potassium chloride and benzalkonium chloride in the disclosed formula. Both veligers and adult mussels are susceptible to these agents, and the two together increase the other's ability to destroy the mussels. This fact can be critical to people who live in areas inhabited by invasive mussels to help keep these mussels from spreading from one body of water to another.

Finally, the last parameter addressed is the removal of surface foam from the water in the holding or transport tank. Surface foam is created from protein in the water and hinders oxygen transfer with air at the surface. The disclosed formula contains about 73 ppm±10% of polysiloxane oil to break the surface tension of the water, and thus hinders the formation of foam.

Experiments with the disclosed formula have proven that all parameters leading to fish fatality in captive tank systems have been addressed with the disclosed formula. A broad selection of proven agents are placed together. The result is a single use formula which provides even the most novice fish handler an increased chance of maintaining and transporting live fish for future use or release. Those of ordinary skill in the art will understand the synergism taking place with the disclosed formula, especially with regard to diseases and invasive species control. Furthermore, by formulating such a complicated compound, fish handlers have been provided with an all-inclusive water conditioner which otherwise would either be totally unavailable or require the use of multiple products to obtain similar results. Studies have proven that the exact use of sodium chloride to potassium chloride to soluble dextrose ratios are particularly critical and are necessary to maintain proper osmotic electrolyte balances in the fish.

Although the disclosed invention has been described with reference to its preferred embodiment, this description is not meant to be construed in a limited sense. Various modifications of the disclosed embodiment, as well as alternative embodiments will become apparent to persons skilled in the art upon the reference to the description of the invention. It is, therefore, contemplated that the appended claims will cover such modifications that fall within the scope of the invention.

What is claimed is:

1. A method of sedating fish during holding and transportation in a tank of water to decrease the fish's reaction of fighting captivity, comprising the step of using about 43 ppm±10% of isoeugenol by weight as the calming agent in the water.

2. The method as defined in claim 1 further including the step of combining about 3647 ppm±10% of electrolyte sodium chloride and about 1458 ppm±10% ppm potassium chloride in ionic form to replace lost electrolytes due to stress in the fish.

3. The method as defined in claim 1 further including the step of adding about 310 ppm±10% soluble dextrose.

4. A method of preserving the life of captive fish in a water tank comprising the step of combining isoeugenol, electrolyte sodium chloride and potassium chloride along with soluble dextrose in the water.

5. The method as defined in claim 4 further including the step of removing the harmful effects of ammonia from the water in the vessel by the use of sodium formaldehyde bisulfite.

6. The method as defined in claim 4 further including the step of detoxifying harmful chlorine.

7. The method as defined in claim 4 further including the step of using Methylene blue and Acriflavine to counter bacterial and fungal diseases.

8. The method as defined in claim 4 further including the step of using benzalkonium chloride and Povidone-iodine.

9. The method as defined in claim 4 further including the step of destroying invasive species such as the Zebra mussel and Quagga mussels by the use of the synergistic effects of potassium chloride and benzalkonium chloride.

10. The method as defined in claim 4 further including the step of introducing aloe vera into the water to protect the natural slime coat of the fish and further enhance anti-bacterial growth in the water.

11. The method as defined in claim 4 further including the step of chelating heavy metals such as mercury, lead, etc. or any pesticides which may be present from runoff in agricultural areas.

12. The method as defined in claim 4 for the including the step of using polysiloxane oil to hinder the formation of surface foam on the water in the holding or transportation vessel.

13. A formula for an additive to be added to a water tank to preserve the life of captive fish contained therein, said formula comprising:
about 43 ppm±10% by weight of isoeugenol;
about 3647 ppm±10% by weight of sodium chloride;
about 1458 ppm±10% by weight potassium chloride;
about 310 ppm±10% by weight of soluble dextrose;
about 456 ppm±10% by weight of an ammonia remover;
about 176 ppm±10% by weight of a chlorine remover;

about 2 ppm±10% by weight of a bacterial and fungal spore remover;

about 0.75 ppm±10% by weight of an anti-columnaris and saprolegnia agent;

about 4.1 ppm±10% by weight of an anti viral agent;

about 10.25 ppm±10% by weight of a disinfectant;

about 2.1 ppm±10% by weight of a chelating agent;

about 8.5 ppm±10% by weight of a chelating agent; and about 73 ppm±10% by weight of a surface foam remover.

14. The formula as defined in claim 13 wherein said ammonia remover is sodium formaldehyde bisulfite.

15. The formula as defined in claim 14 wherein said chlorine remover is sodium thiosulfate.

16. The formula as defined in claim 14 wherein said bacterial and fungal spore remover is methylene blue.

17. The formula as defined in claim 14 wherein said anti-columnaris and saprolegnia agent is acriflavine.

18. The formula as defined in claim 14 wherein said antiviral agent is benzalkonium chloride.

19. The formula as defined in claim 14 wherein said disinfectant is povidone-iodine.

20. The formula as defined in claim 14 wherein said slime coat protecting agent is *aloe vera*.

21. The formula as defined in claim 14 wherein said chelating agent is tetrasodium.

22. The formula as defined in claim 14 wherein said surface foam remover is polysiloxane oil.

* * * * *